(12) United States Patent
Grainger et al.

(10) Patent No.: US 8,497,261 B2
(45) Date of Patent: *Jul. 30, 2013

(54) 3-AMINOCAPROLACTAM COMPOUNDS FOR TREATING INFLAMMATORY DISORDERS

(75) Inventors: David J. Grainger, Cambridge (GB); David John Fox, Coventry (GB)

(73) Assignee: Cambridge Enterprise Limited, Cambridge (GB)

(*) Notice: Subject to any disclaimer, the term of this patent is extended or adjusted under 35 U.S.C. 154(b) by 411 days.
This patent is subject to a terminal disclaimer.

(21) Appl. No.: 12/726,311

(22) Filed: Mar. 17, 2010

(65) Prior Publication Data
US 2010/0292213 A1 Nov. 18, 2010

Related U.S. Application Data

(62) Division of application No. 11/573,637, filed as application No. PCT/GB2005/003133 on Aug. 10, 2005, now Pat. No. 7,691,845.

(30) Foreign Application Priority Data

Aug. 11, 2004 (GB) .................................. 0417863.8

(51) Int. Cl.
*A61K 31/55* (2006.01)
*C07D 223/10* (2006.01)
*A61P 29/00* (2006.01)
*A61P 19/10* (2006.01)

(52) U.S. Cl.
USPC ..................................... 514/212.03; 540/527

(58) Field of Classification Search
None
See application file for complete search history.

(56) References Cited

U.S. PATENT DOCUMENTS
5,155,102 A 10/1992 Giannessi et al.

FOREIGN PATENT DOCUMENTS
EP 093949 11/1983
EP 1717225 A1 11/2006
JP 09087331 3/1997
JP 2003146972 5/2003
WO 9828300 A1 7/1998
WO 2004022536 3/2004
WO 200507790 A1 8/2005
WO 2006016152 2/2006

OTHER PUBLICATIONS

Nenajdenko et al.: Russian Chemical Bulletin, Int. Ed. 52(11): 2473-2482, 2003.
"International Search Report in Application No. PCT/GB2005/003133", (Jan. 18, 2006).
"STN CHEMCATS database, Accession No. 2004:3652767 & Ambinter Stocik Screening Collection Catalogue (published Jan. 1, 2004) RN 700815-65-2".
Angelucci, L, et al., "Synthesis and amnesia-reversal activity of a series of 7- and 5- membered 3-acylamino lactams", Journal of Medical Chemistry, 36(11), (May 28, 1993), 1511-1519.
Weiss, Benjamin, et al., "Effects of Various amides on a rat brain puromycin-sensitive aminopeptidase and on induced convulsions in mice", (1992), 153-59.

*Primary Examiner* — Bong-Sook Baek
(74) *Attorney, Agent, or Firm* — VLP Law Group LLP; Richard G. A. Bone

(57) ABSTRACT

The invention provides compounds, compositions and uses of compounds of general formula (I) or pharmaceutically acceptable salts thereof, which are 3-aminocaprolactam derivatives, for the preparation of a medicament intended to treat an inflammatory disorder:

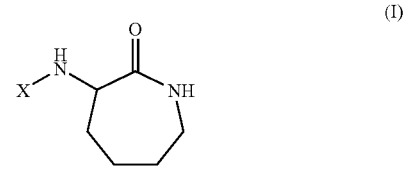

(I)

wherein
X is $-CO-Y-(R^1)_n$ or $SO_2-Y-(R^1)_n$; and
Y is a cycloalkyl or polycycloalkyl group (such as an adamantyl, adamantanemethyl, bicyclooctyl, cyclohexyl, cyclopropyl group);
or is a cycloalkenyl or polycycloalkenyl group.

22 Claims, 1 Drawing Sheet

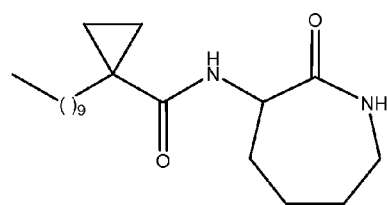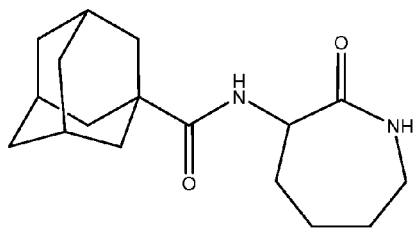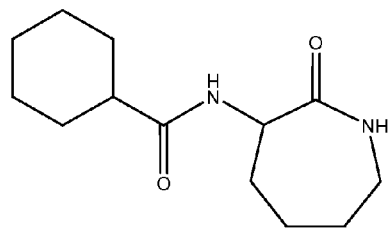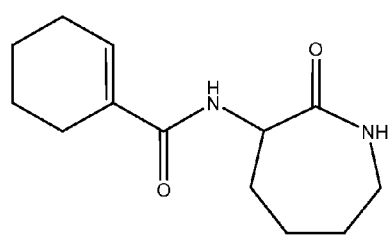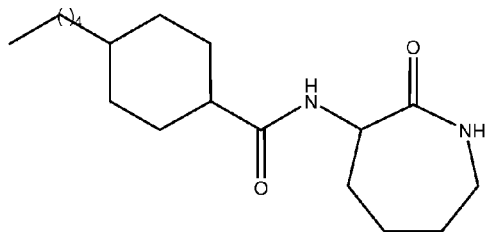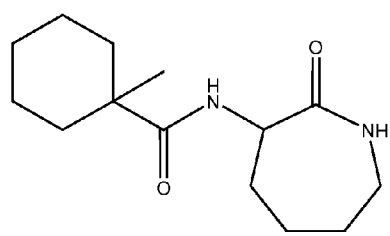

3-AMINOCAPROLACTAM COMPOUNDS FOR TREATING INFLAMMATORY DISORDERS

This application is a divisional of U.S. application Ser. No. 11/573,637, now U.S. Pat. No. 7,691,845, which is the National Stage of International Application No. PCT/GB2005/003133, filed Aug. 10, 2005, which claims the benefit under 35 U.S.C. §119 of United Kingdom application serial number 0417863.8, filed Aug. 11, 2004. The disclosures of the prior applications are incorporated by reference in the disclosure of this application.

The invention relates to the use of 3-aminocaprolactam derivatives for preparing a medicament intended to prevent or treat inflammatory disorders.

Inflammation is an important component of physiological host defence. Increasingly, however, it is clear that temporally or spatially inappropriate inflammatory responses play a part in a wide range of diseases, including those with an obvious leukocyte component (such as autoimmune diseases, asthma or atherosclerosis) but also in diseases that have not traditionally been considered to involve leukocytes (such as osteoporosis or Alzheimer's disease).

The chemokines are a large family of signalling molecules with homology to interleukin-8 which have been implicated in regulating leukocyte trafficking both in physiological and pathological conditions. With more than fifty ligands and twenty receptors involved in chemokine signalling, the system has the requisite information density to address leukocytes through the complex immune regulatory processes from the bone marrow, to the periphery, then back through secondary lymphoid organs. However, this complexity of the chemokine system has at first hindered pharmacological approaches to modulating inflammatory responses through chemokine receptor blockade. It has proved difficult to determine which chemokine receptor(s) should be inhibited to produce therapeutic benefit in a given inflammatory disease.

More recently, a family of agents which block signalling by a wide range of chemokines simultaneously has been described: Reckless et al., Biochem J. (1999) 340:803-811. The first such agent, a peptide termed "Peptide 3", was found to inhibit leukocyte migration induced by 5 different chemokines, while leaving migration in response to other chemoattractants (such as fMLP or TGF-beta) unaltered. This peptide, and its analogs such as NR58-3.14.3 (i.e. Sequence ID No. 1 c(DCys-DG1n-DIle-DTrp-DLys-DG1n-DLys-DPro-DAsp-DLeu-DCys)-NH$_2$), are collectively termed "Broad Spectrum Chemokine Inhibitors" (BSCIs). Grainger et al., Biochem. Pharm. 65 (2003) 1027-1034 have subsequently shown BSCIs to have potentially useful anti-inflammatory activity in a range of animal models of diseases. Interestingly, simultaneous blockade of multiple chemokines is not apparently associated with acute or chronic toxicity, suggesting this approach may be a useful strategy for developing new anti-inflammatory medications with similar benefits to steroids but with reduced side-effects.

However, peptides and peptoid derivatives such as NR58-3.14.3, may not be optimal for use in vivo. They are quite expensive to synthesise and have relatively unfavourable pharmacokinetic and pharmacodynamic properties. For example, NR583.14.3 is not orally bioavailable and is cleared from blood plasma with a half-life period of less than 30 minutes after intravenous injection.

Two parallel strategies have been adopted to identify novel preparations which retain the anti-inflammatory properties of peptide 3 and NR58-3.14.3, but have improved characteristics for use as pharmaceuticals. Firstly, a series of peptide analogs have been developed, some of which have longer plasma half-lives than NR58-3.14.3 and which are considerably cheaper to synthesise. Secondly, a detailed structure: activity analysis of the peptides has been carried out to identify the key pharmacophores and design small non-peptidic structures which retain the beneficial properties of the original peptide.

This second approach yielded several structurally distinct series of compounds which retained the anti-inflammatory properties of the peptides, including 16-amino and 16-aminoalkyl derivatives of the alkaloid yohimbine, as well as a range of N-substituted 3-aminoglutarimides. (Reference: Fox et al., J Med Chem 45 (2002) 360-370: WO 99/12968 and WO 00/42071.) All of these compounds are broad-spectrum chemokine inhibitors which retain selectivity over non-chemokine chemoattractants, and a number of them have been shown to block acute inflammation in vivo.

The most potent and selective of these compounds was (S)-3-(undec-10-enoyl)-aminoglutarimide (NR58,4), which inhibited chemokine-induced migration in vitro with an $ED_{50}$ of 5 nM. However, further studies revealed that the aminoglutarimide ring was susceptible to enzymatic ring opening in serum. Consequently, for some applications (for example, where the inflammation under treatment is chronic, such as in autoimmune diseases) these compounds may not have optimal properties, and a more stable compound with similar anti-inflammatory properties may be superior.

As an approach to identifying such stable anlogs, various derivatives of (S)-3-(undec-10-enoyl)-aminoglutarimide have been tested for their stability in serum. One such derivative, the 6-deoxo analog (S)-3-(undec-10-enoyl)-tetrahydropyridin-2-one, is completely stable in human serum for at least 7 days at 37° C., but has considerably reduced potency compared with the parental molecule.

Amide derivatives of 3-aminocaprolactam have already been disclosed in the art. For example:

Japanese patent application No. 09087331 describes 3-aminocaprolactam amide derivatives wherein the amide alkyl side chain may contain from 2 to 30 carbon atoms. These compounds have been presented as oil-gelating agents.

U.S. Pat. No. 6,395,282 describes immunogenic conjugates comprising a carrier molecule coupled to an auto-inducer of a Gram negative bacteria, wherein said auto-inducer can be a 3-aminocaprolactam amide derivative wherein the amide alkyl side chain may contain up to 34 carbon atoms. However, a therapeutic use is disclosed only for the conjugates and not for the isolated amide derivative.

An article by Weiss et al. (*Research Communications in Psychology, Psychiatry and Behavior* (1992), 17(3-4), 153-159) discloses a series of 3-aminocaprolactam amide derivatives, and among others 3-hexanamido-DL-ϵ-caprolactam and 3-dodecanamido-DL-ϵ-caprolactam. These compounds are presented as having only an in vitro activity but no significant in vivo effect.

In other words, though some alkyl amide derivatives of 3-aminocaprolactam have certainly been known in the art, no actual pharmaceutical use has been described for 3-aminocaprolactam amide derivatives.

The invention provides the use of a compound of general formula (I), or a pharmaceutically acceptable salt thereof, for the preparation of a medicament intended to treat inflammatory disorder:

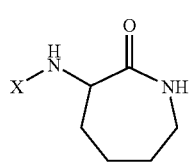

(I)

wherein

X is —CO—Y—(R$^1$)$_n$ or SO$_2$—Y—(R$^1$)$_n$;

Y is a cycloalkyl or polycyloalkyl group (such as an adamantyl, adamantanemethyl, bicyclooctyl, cyclohexyl, cyclopropyl group);

or is a cycloalkenyl or polycycloalkenyl group;

each R$^1$ is independently selected from hydrogen or an alkyl, haloalkyl, alkoxy, haloalkoxy, alkenyl, alkynyl or alkylamino radical of 1 to 20 carbon atoms (for example of 5 to 20 carbon atoms, of 8 to 20 carbon atoms, of 9 to 20 carbon atoms, of 10 to 18 carbon atoms, of 12 to 18 carbon atoms, of 13 to 18 carbon atoms, of 14 to 18 carbon atoms, of 13 to 17 carbon atoms);

or each R$^1$ is independently selected from fluoro, chloro, bromo, iodo, hydroxy, oxyalkyl, amino, aminoalkyl or aminodialkyl radical; and n is any integer from 1 to m, where m is the maximum number of substitutions permissible on the cyclo-group Y.

Alternatively R$^1$ may be selected from a peptido radical, for example having from 1 to 4 peptidic moieties linked together by peptide bonds (for example a peptido radical of 1 to 4 amino acid residues).

The carbon atom at position 3 of the caprolactam ring is asymmetric and consequently, the compounds according to the present invention have two possible enantiomeric forms, that is, the "R" and "S" configurations. The present invention encompasses the two enantiomeric forms and all combinations of these forms, including the racemic "RS" mixtures. With a view to simplicity, when no specific configuration is shown in the structural formulae, it should be understood that the two enantiomeric forms and their mixtures are represented.

Preferably, the compounds of general formula (I) or pharmaceutically acceptable salts thereof used according to this aspect of the invention will be compounds of general formula (I')

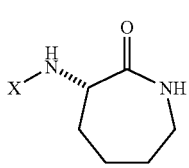

(I')

wherein X has the same meaning as above.

Preferably, the compounds of general formula (I) or (I'), or their pharmaceutically acceptable salts, will be such that the ring or rings of Y constrain the bond angles at the alpha-carbon to be essentially tetrahedral (i.e. sp3 hybrid bonds). The "alpha carbon" is either at the 2-position (relative to the amide carbonyl) or at the 1-position (relative to the sulfonamide sulfonyl group).

Any substituent R$^1$ may be a substituent at any permissible position on the ring or rings of the cyclo-group Y. In particular it is to be noted that the invention includes compounds in which the "alpha carbon" is both part of the cyclo group and is itself substituted. The definition of (R$^1$)$_n$ encompasses compounds of the invention with no substitution (i.e. R$^1$=hydrogen), compounds of the invention with mono substitution (i.e. R$^1$ is not hydrogen and n=1), and also multiple substitution (i.e. at least two R$^1$ groups are not hydrogen and n=2 or more).

The invention also provides pharmaceutical compositions comprising, as active ingredient, a compound of general formula (I), or a pharmaceutically acceptable salt thereof, and at least one pharmaceutically acceptable excipient and/or carrier:

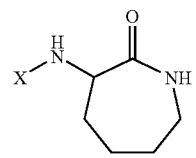

(I)

wherein

X is —CO—Y—(R$^1$)$_n$ or SO$_2$—Y—(R$^1$)$_n$;

Y is a cycloalkyl or polycyloalkyl group (such as an adamantyl, adamantanemethyl, bicyclooctyl, cyclohexyl, cyclopropyl group);

or is a cycloalkenyl or polycycloalkenyl group;

each R$^1$ is independently selected from hydrogen or an alkyl, haloalkyl, alkoxy, haloalkoxy, alkenyl, alkynyl or alkylamino radical of 1 to 20 carbon atoms (for example of 5 to 20 carbon atoms, of 8 to 20 carbon atoms, of 9 to 20 carbon atoms, of 10 to 18 carbon atoms, of 12 to 18 carbon atoms, of 13 to 18 carbon atoms, of 14 to 18 carbon atoms, of 13 to 17 carbon atoms);

or each R$^1$ is independently selected from fluoro, chloro, bromo, iodo, hydroxy, oxyalkyl, amino, aminoalkyl or aminodialkyl radical; and n is any integer from 1 to m, where m is the maximum number of substitutions permissible on the cyclo-group Y.

Alternatively R$^1$ may be selected from a peptido radical, for example having from 1 to 4 peptidic moieties linked together by peptide bonds (for example a peptido radical of 1 to 4 amino acid residues).

Preferably, the compounds of general formula (I) or pharmaceutically acceptable salts thereof used according to this aspect of the invention will be compounds of general formula (I')

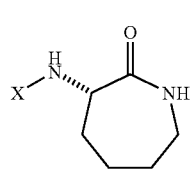

(I')

wherein X has the same meaning as above.

By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention also provides compounds and salts thereof of general formula (I)

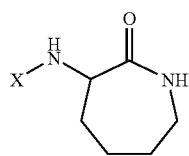

(I)

wherein
X is —CO—Y—(R$^1$)$_n$ or SO$_2$—Y—(R$^1$)$_n$;
Y is a cycloalkyl or polycyloalkyl group (such as an adamantyl, adamantanemethyl, bicyclooctyl, cyclohexyl, cyclopropyl group);
or is a cycloalkenyl or polycycloalkenyl group;
each R$^1$ is independently selected from hydrogen or an alkyl, haloalkyl, alkoxy, haloalkoxy, alkenyl, alkynyl or alkylamino radical of 1 to 20 carbon atoms (for example of 5 to 20 carbon atoms, of 8 to 20 carbon atoms, of 9 to 20 carbon atoms, of 10 to 18 carbon atoms, of 12 to 18 carbon atoms, of 13 to 18 carbon atoms, of 14 to 18 carbon atoms, of 13 to 17 carbon atoms);
or each R$^1$ is independently selected from fluoro, chloro, bromo, iodo, hydroxy, oxyalkyl, amino, aminoalkyl or aminodialkyl radical; and
n is any integer from 1 to m, where m is the maximum number of substitutions permissible on the cyclo-group Y.

Alternatively R$^1$ may be selected from a peptido radical, for example having from 1 to 4 peptidic moieties linked together by peptide bonds (for example a peptido radical of 1 to 4 amino acid residues).

Preferably, the compounds of general formula (I) or salts thereof used according to this aspect of the invention will be compounds of general formula (I')

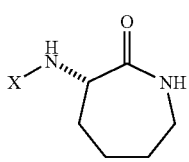

(I')

wherein X has the same meaning as above.

Preferably, the compounds of general formula (I) or (I') when used in the invention, or their salts, will be such that the ring or rings of Y constrain the bond angles at the alpha-carbon to be essentially tetrahedral (i.e. sp3 hybrid bonds).

In particular, preferred compounds of general formula (I) or (I') and their salts according to any aspect of the present invention are selected from the group consisting of:
(S)-3-(Cyclohexanecarbonyl)amino-caprolactam;
(S)-3-(1'-methylcyclohexanecarbonyl)amino-caprolactam;
(S)-3-(Cyclohex-1'-enecarbonyl)amino-caprolactam;
(S)-3-(trans-4'-pentylcyclohexane-1-carbonyl)amino-caprolactam;
(S)-3-(4'-pentyl[2,2,2]bicyclo-octane-1-carbonyl)amino-caprolactam;
(S)-3-(1'-Adamantanecarbonyl)amino-caprolactam;
(S)-3-(1'-Adamantanylmethanecarbonyl)amino-caprolactam;
(S)-3-(3'-chloro-1'-adamantanecarbonyl)amino-caprolactam;
(S)-3-(3',5'-Dimethyl-1'-adamantanecarbonyl)amino-caprolactam;
(S)-3-(3',5',7'-Trimethyl-1'-adamantanecarbonyl)amino-caprolactam;
and the salts thereof.

The most preferred compound is (S)-3(1'-Adamantanecarbonyl)amino-caprolactam and salts thereof.

The invention also provides the sulfonamide analogues of the exemplified compounds: i.e. the sulfonyl-amino-caprolactam equivalents of the said compounds.

As mentioned in the discussion of prior art above, certain alkyl amide derivatives of 3-amino caprolactam may be known as compounds per se (though it is not presently known that any have been described as such as pharmaceutical compositions or for medical use in an anti-inflammatory context).

The invention includes compounds, compositions and uses thereof as defined, wherein the compound is in hydrated or solvated form.

The amide derivatives of 3-aminocaprolactam described here are functional BSCIs. They are relatively inexpensive to synthesise, using facile synthesis routes provided herein; they are stable in human serum and consequently have excellent pharmacokinetic properties; they are orally bioavailable; they are highly potent broad-spectrum chemokine inhibitors in vitro with excellent selectivity over non-chemokine chemoattractants; they are highly potent and effective anti-inflammatory agents in vivo in rodent models of inflammation; their administration is not associated with any significant acute toxicity at the doses necessary to achieve a maximal therapeutic effect. Taken together, these properties suggest that amide derivatives of 3-aminocaprolactam represent anti-inflammatory medications with advantages over previously described compounds.

In comparison to the prior art the improvement of the present invention lies in the provision of the 3-aminocaprolactam moiety with a side chain having one or more alkyl/alkenyl rings to constrain the bond angles at the alpha carbon of the side chain. Compounds of this invention are significantly superior to compounds with linear alkyl chains (whether alkyl amides or alkyl sulfonamides).

Prior art peptides (such as NR58-3.14.3) have the disadvantages that: (a) they are expensive and require solid phase synthesis (at least for the longer ones) and (b) they clear very quickly via the kidneys and (c) they are generally less potent.

The prior art aminoglutarimides are cheap, not cleared quickly via the kidneys and more potent BUT they do not show metabolic stability.

The improvement described here, the aminocaprolactams, are cheap, not cleared by the kidney and even more potent, and are also metabolically stable.

According to this invention, inflammatory disorders intended to be prevented or treated by the compounds of general formula (I) or (I') or the pharmaceutically acceptable salts thereof or pharmaceutical compositions or medicaments containing them as active ingredients include notably:

- autoimmune diseases, for example such as multiple sclerosis;
- vascular disorders including stroke, coronary artery diseases, myocardial infarction, unstable angina pectoris, atherosclerosis or vasculitis, e.g., Behcet's syndrome, giant cell arteritis, polymyalgia rheumatica, Wegener's granulomatosis, Churg-Strauss syndrome vasculitis, Henoch-Schönlein purpura and Kawasaki disease;
- viral infection or replication, e.g. infections due to or replication of viruses including pox virus, herpes virus (e.g., Herpesvirus saimiri), cytomegalovirus (CMV) or lentivirus;
- asthma;
- osteoporosis; (low bone mineral density);
- tumor growth;
- rheumatoid arthritis;
- organ transplant rejection and/or delayed graft or organ function, e.g. in renal transplant patients;
- a disorder characterised by an elevated TNF-α level;
- psoriasis;
- skin wounds;
- disorders caused by intracellular parasites such as malaria or tuberculosis;
- allergies; or
- Alzheimer's disease.

According to this invention, further inflammatory disorders include:

- ALS;
- fibrosis (particularly pulmonary fibrosis, but not limited to fibrosis in the lung);
- the formation of adhesions (particularly in the peritoneum and pelvic region);
- antigen induced recall response;
- immune response suppression.

These clinical indications fall under the general definition of inflammatory disorders or disorders characterized by elevated TNFα levels.

Where legally permissible, the invention also provides a method of treatment, amelioration or prophylaxis of the symptoms of an inflammatory disease (including an adverse inflammatory reaction to any agent) by the administration to a patient of an anti-inflammatory amount of a compound, composition or medicament as claimed herein.

Administration of a medicament according to the invention can be carried out by topical, oral, parenteral route, by intramuscular injection, etc.

The administration dose envisaged for a medicament according to the invention is comprised between 0.1 mg and 10 g depending on the type of active compound used.

According to the invention, the compounds of general formula (I) or (I') can be prepared using the processes described hereafter.

Preparation of the Compounds of General Formula (I) or (I')

All the compounds of general formula (I') or (I') can be prepared easily according to general methods known to the person skilled in the art.

Nevertheless, the following preferred synthetic route is proposed:

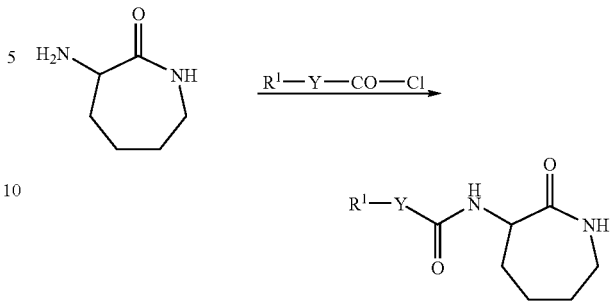

Diagram 1

The reaction shown in Diagram 1 may be carried out, for example, in chloroform or dichloromethane. The most preferred reaction solvent is dichloromethane.

The above reaction is preferably carried out in the presence of a base, for example $Na_2CO_3$.

The above reaction may be carried out at ambient temperature (about 25° C.) or more generally at a temperature between 20 and 50° C.

Definitions

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 1 to 20 carbon atoms specified in respect of (inter alia) formula I is intended to include all integers between 4 and 20 and all sub-ranges of each combination of upper and lower numbers, whether exemplified explicitly or not.

As used herein, the term "comprising" is to be read as meaning both comprising and consisting of: Consequently, where the invention relates to a "pharmaceutical composition comprising as active ingredient" a compound, this terminology is intended to cover both compositions in which other active ingredients may be present and also compositions which consist only of one active ingredient as defined.

The term "peptidic moieties" used herein is intended to include the following 20 naturally-occurring proteogenic amino acid residues:

| SYMBOL: | MEANING |
|---------|---------|
| Ala | Alanine |
| Cys | Cysteine |
| Asp | Aspartic Acid |
| Glu | Glutamic Acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |

-continued

| SYMBOL: | MEANING |
|---|---|
| Thr | Threonine |
| Val | Valine |
| Trp | Tryptophan |
| Tyr | Tyrosine |

Modified and unusual amino acid residues, as well as peptido-mimetics, are also intended to be encompassed within the definition of "peptidic moieties".

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the above procedures and should in no way be considered to limit the scope of the invention.

FIGURES

FIG. 1 shows the chemical structure of examples of compounds according to the invention.

EXAMPLES

General Procedure for the Synthesis of the Starting Compounds

The hydrochlorides of (R) and (S)-3-amino-caprolactam, and the hydro-pyrrolidine-5-carboxylates of (R,R) and (S,S)-3-amino-caprolactam were synthesised according to literature (cf. Boyle et al., *J. Org. Chem.*,(1979), 44, 4841-4847; Rezler et al., *J. Med. Chem.* (1997), 40, 3508-3515).

Example 1

(S)-3-(Cyclohexanecarbonyl)amino-caprolactam (S,S)-3-amino-caprolactam hydro-pyrrolidine-5-carboxylate 2 (5 mmol) and $Na_2CO_3$ (15 mmol) in water (25 ml) were added to a solution of cyclohexanecarbonyl chloride (5 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by recrystallisation from EtOAc/hexane to give the lactam (540 mg, 45%); m.p. (EtOAc/hexanes) 180-181° C.; $[\alpha]_D^{25}$ (c=1, $CHCl_3$)+42.0; $v_{max}/cm^{-1}$ 3294 (NH), 1668, 1614 (CO), 1537 (NH); $\delta_H$(500 MHz, $CDCl_3$) 6.89 (1H, d, J 5.5, CHNH), 6.51 (1H, br s, $CH_2NH$), 4.48 (1H, dd, J 11, 6, CHNH), 3.30-3.17 (2H, m, $CH_2NH$), 2.11 (1H, tt, J 11.5, 3.5, ($CH_2$)CHCO), 2.01 (1H, br d, J 13, lactam ring CH), 1.98-1.92 (1H, m, lactam ring CH), 1.87-1.70 (6H, m, lactam ring CH×2+cyhex CH×4), 1.66-1.59 (1H, m, cyhex CH), 1.47-1.30 (4H, br m, lactam ring CH×2+cyhex CH×2) and 1.23-1.15 (3H, m, cyhex CH×3); $\delta_C$ (125 MHz, $CDCl_3$) 175.9, 175.3 (CO), 51.8 (NHCHCO), 45.2 (CH), 42.1, 31.7, 29.6, 29.4, 28.9, 27.9, 25.7 (×2), 25.6 ($CH_2$); m/z ($M^+C_{13}H_{22}N_2O_2$ requires 238.16813) 238.16768.

Example 2

(S)-3-(1'-methylcyclohexanecarbonyl)amino-caprolactam (S,S)-3-amino-caprolactam hydro-pyrrolidine-5-carboxylate 2 (5 mmol) and $Na_2CO_3$ (15 mmol) in water (25 ml) were added to a solution of 1-methylcyclohexanecarbonyl chloride (5 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by recrystallisation from EtOAc/hexane to give the lactam (540 mg, 43%); m.p. (EtOAc/hexanes) 168-169° C.; $[\alpha]_D^{25}$ (c=1, $CHCl_3$)+33.0; $v_{max}/cm^{-1}$ 3380, 3241 (NH), 1674, 1638 (CO), 1501 (NH); $\delta_H$(500 MHz, $CDCl_3$) 7.12 (1H, d, J5, CHNH), 6.52 (1H, br s, $CH_2NH$), 4.48 (1H, ddd, J 11, 5.5, 1.5 CHNH), 3.30-3.16 (2H, m, $CH_2NH$), 2.01 (1H, br d, J 13, lactam ring CH), 1.98-1.86 (3H, m, lactam ring CH+cyhex CH×2), 1.85-1.73 (2H, m, lactam ring CH×2), 1.56-1.47 (2H, m, cyhex CH×2), 1.47-1.33 (5H, br m, lactam ring CH×2+cyhex CH×3) and 1.33-1.25 (3H, m, cyhex CH×3); $\delta_C$ (125 MHz, $CDCl_3$) 176.9, 167.0 (CO), 52.0 (NHCHCO), 42.5 (C quat), 42.1, 35.5 (×2), 31.6, 28.9, 27.9 ($CH_2$), 26.4 ($CH_3$), 25.8, 22.9 (×2) ($CH_2$); m/z ($M^+C_{14}H_{24}N_2O_2$ requires 252.18378) 252.18323.

Example 3

(S)-3-(Cyclohex-1'-enecarbonyl)amino-caprolactam (S,S)-3-amino-caprolactam hydro-pyrrolidine-5-carboxylate 2 (5 mmol) and $Na_2CO_3$ (15 mmol) in water (25 ml) were added to a solution of cyclohex-1-ene-1-carbonyl chloride (5 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by recrystallisation from EtOAc/hexanes to give the lactam (431 mg, 36%); m.p. (EtOAc/hexanes) 151-152° C.; $[\alpha]_D^{25}$ (c=1, $CHCl_3$)+57.5; $v_{max}/cm^{-1}$ 3219 (NH), 1652, 1628 (C=O, C=C), 1515 (NH); $\delta_H$ (500 MHz, $CDCl_3$) 7.12 (1H, d, J5, CHNH), 6.67 (1H, qn, J 1.5, CH=C), 6.52 (1H, br s, $CH_2NH$), 4.54 (1H, ddd, J 11, 5.5, 1.5 CHNH), 3.32-3.18 (2H, m, $CH_2NH$), 2.30-2.17 (2H, m, $CH_2CH=C$), 2.16-2.10 (2H, m, CH=$CCH_2$), 2.07 (1H, br d, J 15, lactam ring CH), 2.00-1.92 (1H, m, lactam ring CH), 1.87-1.76 (2H, m, lactam ring CH×2), 1.68-1.60 (2H, m, cyhex CH×2), 1.60-1.52 (2H, m, cyhex CH×2) and 1.50-1.31 (2H, br m, lactam ring CH×2); $\delta_C$ (125 MHz, $CDCl_3$) 175.9, 167.4 (CO), 134.0 (CH=C), 132.8 (CH=C), 52.1 (NHCHCO), 42.1, 31.6, 28.9, 27.9, 25.3, 24.0, 22.1, 21.5 ($CH_2$); m/z ($M^+C_{13}H_{20}N_2O_2$ requires 236.15248) 236.15208.

Example 4

(S)-3-(trans-4'-pentylcyclohexane-1-carbonyl)amino-caprolactam (S,S)-3-amino-caprolactam hydro-pyrrolidine-5-carboxylate 2 (7 mmol) and $Na_2CO_3$ (21 mmol) in water (25 ml) were added to a solution of trans-4-pentylcyclohexane-1-carbonyl chloride (6 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by recrystallisation from EtOAc/hexane to give the lactam (977 mg, 53%); m.p. 182-184° C.; $[\alpha]_D^{25}$ (c=1, $CHCl_3$)+32.2; $v_{max}/cm^{-1}$ 3326 (NH), 1670, 1636 (CO), 1511 (NH); $\delta_H$(500 MHz, $CDCl_3$) 6.91 (1H, d, J 5.5, CHNH), 6.87-6.70 (1H, br m, $CH_2NH$), 4.44 (1H, ddd, J 11, 6.0, 1.5, CHNH), 3.28-3.15 (2H, m, $CH_2NH$), 2.08-1.90 (3H, br m, ring CH×2+$(CH_2)_2$CHCO), 1.88-1.72 (6H, m, ring CH+chain $CH_2$×4), 1.45-1.28 (4H, br m, ring CH+chain $CH_2$×2+chain $CH(CH_2)_3$), 1.27-1.07 (9H, br m, ring CH+chain $CH_2$×8) and 0.90-0.79 (5H, m, chain $CH_2+CH_3$); $\delta_C$ (125 MHz, $CDCl_3$) 176.0, 175.3 (CO), 51.8 (NHCHCO), 45.4 (CH), 41.0 ($CH_2$), 37.1 ($CH_2$), 36.9 (CH), 32.5, 32.4, 32.1, 31.7, 29.6, 29.4, 28.9, 27.9, 26.5, 22.6 ($CH_2$) and 14.0 ($CH_3$); m/z ($M^+C_{18}H_{32}N_2O_2$ requires 308.24638) 308.24566.

Example 5

(S)-3-(4'-pentyl[2,2,2]bicyclo-octane-1-carbonyl) amino-caprolactam (S,S)-3-amino-caprolactam hydro-pyrrolidine-5-carboxylate 2 (5.5 mmol) and $Na_2CO_3$ (16.5 mmol) in water (25 ml) were added to a solution of trans-4-pentylcyclohexane-1-carbonyl chloride (4.4 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by recrystallisation from EtOAc/hexane to give the lactam (868 mg, 57%); m.p. 195-196° C.; $[\alpha]_D^{25}$ (c=1, $CHCl_3$)+28.7; $v_{max}/cm^{-1}$3395, 3254 (NH), 1677, 1626 (CO), 1501 (NH); $\delta_H$(500 MHz, $CDCl_3$) 6.98 (1H, d, J 5.5, CHNH), 6.77-6.63 (1H, br m, $CH_2NH$), 4.41 (1H, dd, J 11, 5.5, CHNH), 3.27-3.15 (2H, m, $CH_2NH$), 2.00-1.88 (2H, br m, ring CH×2), 1.81-1.73 (2H, br m, ring CH×2), 1.69 (1H, br t, J7.5, chain $CCH_2CH_2C$×6), 1.43-1.30 (8H, br m, ring CH×2+chain $CCH_2CH_2C$×6), 1.24 (2H, sext, J 7, $CH_2CH_3$), 1.19-1.07 (4H, m, $CH_2CH_2CH_2CH_3$) 1.05-0.98 (2H, m, $CH_2Bu$) and 0.82 (3H, t, J 7, $CH_3$); $\delta_C$ (125 MHz, $CDCl_3$) 177.4, 176.1 (CO), 51.9 (NHCHCO), 42.0, 41.2 ($CH_2$), 39.0 (C quat), 32.7, 31.6, 30.6 (×3) ($CH_2$), 30.4 (C quat), 28.9, 28.8 (×3), 27.9, 23.3, 22.6 ($CH_2$) and 14.0 ($CH_3$); m/z ($M^+C_{20}H_{34}N_2O_2$ requires 334.26203) 334.26352.

Example 6

(S)-3-(1'-Adamantanecarbonyl)amino-caprolactam (S)-3-amino-caprolactam hydrochloride 2 (1 mmol) and $Na_2CO_3$ (3 mmol) in water (15 ml) were added to a solution of 1-adamantanecarbonyl chloride (1 mmol) in dichloromethane (15 ml) at ambient temperature and the reaction was stirred for 2 hours. The organic layer was then separated and the aqueous phase was extracted with additional dichloromethane (2×25 ml). The combined organic layers were dried over $Na_2CO_3$ and reduced in vacuo. The residue was recrystallised from $CH_2Cl_2$/hexanes to give (S)-3-(1'-adamantanecarbonyl)amino-caprolactam (171 mg, 59%); m.p. 256-258° C.; $[\alpha]_D^{25}$ (c=1, $CHCl_3$)+29.5; $v_{max}/cm^{-1}$3411, 3259 (NH), 1678, 1626 (CO), 1505 (NH); $\delta_H$ (500 MHz, $CDCl_3$) 7.08 (1H, d, J5.5, CHNH), 6.67 (1H, br s, $CH_2NH$), 4.47 (1H, ddd, J 11, 5.5, 1.5, CHNH), 3.32-3.17 (2H, m, $CH_2NH$), 2.06-1.94 (5H, m, 2×ring CH+3×adamantane CH), 1.90-1.75 (8H, m, 2×ring CH+3×adamantane $CH_2$), 1.72 (3H, br d, J 14.5, 3×adamantane CHH), 1.68 (3H, br d, J 14.5, 3×adamantane CHH) and 1.47-1.32 (2H, m, 2×ring CH); $\delta_C$ (125 MHz, $CDCl_3$) 177.2, 175.9 (CO), 51.9 (NHCHCO), 42.2 ($CH_2N$), 40.5 (CCO), 39.0 (3×$CH_2$ adamantane), 36.5 (3×$CH_2$ adamantane), 31.7, 28.9, 28.0 ($CH_2$ lactam), 28.1 (3×CH adamantane); m/z ($MH^+C_{17}H_{27}N_2O_2$ requires 291.2073) 291.1994.

Example 7

(S)-3-(1'-Adamantanylmethanecarbonyl)amino-caprolactam (S)-3-amino-caprolactam hydrochloride 2 (4 mmol) and $Na_2CO_3$ (12 mmol) in water (50 ml) were added to a solution of 1-adamantanemethanecarbonyl chloride (4 mmol) in dichloromethane (50 ml) at ambient temperature and the reaction was stirred for 2 hours. The organic layer was then separated and the aqueous phase was extracted with additional dichloromethane (2×50 ml). The combined organic layers were dried over $Na_2SO_4$ and reduced in vacuo. The residue was recrystallised from EtOAc/hexane to give (S)-3-(1'-adamantanylmethanecarbonyl)amino-caprolactam, recrystallised from EtOAc to give white crystals (688 mg, 56%); m.p. 258-260° C.; $[\alpha]_D^{25}$ (c=1, $CHCl_3$)+30.7; $v_{max}/cm^{-1}$-3409, 3255 (NH), 1682, 1611 (CO), 1539 (NH); $\delta_H$ (500 MHz, $CDCl_3$) 6.82 (1H, d, J5.5, CHNH), 6.77 (1H, br t, J 5.5, $CH_2NH$), 4.48 (1H, ddd, J 11, 6, 1.5, CHNH), 3.28-3.14 (2H, m, $CH_2NH$), 2.04 (1H, br d, J 13.5, C-4H), 1.97-1.86 (6H, m, C-5H+3×adamantane CH+$CH_2CO$), 1.84-1.72 (2H, m, C-5H+C-6H), 1.63 (3H, br d, J 12, adamantane 3×$CH_2$), 1.60-1.54 (9H, m, 9×adamantane $CH_2$) and 1.47-1.27 (2H, m, C-4 H+C-6H); $\delta_C$ (125 MHz, $CDCl_3$) 175.9 (lactam CO), 170.1 (amide CO), 52.0 (NHCHCO), 51.4 ($CH_2CO$), 42.6 (3× adamantane $CH_2$), 42.0 ($NCH_2$), 36.7 (3×$CH_2$ adamantane), 32.7 ($C_{quat}$, adamantane), 31.7 (C-4), 28.8 (C-6), 28.6 (3×CH adamantane), 28.5 (C-5); m/z ($M^+C_{18}H_{28}N_2O_2$ requires 304.2151) 304.21430.

Example 8

(S)-3-(3'-chloro-1'-adamantanecarbonyl)amino-caprolactam (S)-3-amino-caprolactam hydrochloride 2 (3 mmol) and $Na_2CO_3$ (9 mmol) in water (15 ml) were added to a solution of 3-chloro-1-adamantanecarbonyl chloride (3 mmol) in dichloromethane (15 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was recrystallised from EtOAc/Hexane to give (S)-3-(3'-chloro-1'-adamantanecarbonyl)amino-caprolactam (621 mg, 64%); m.p. 204-206° C.; $[\alpha]_D^{25}$ (c=0.5, $CHCl_3$)+26.2; $v_{max}/cm^{-1}$ 3411, 3267 (NH), 1679, 1630 (CO), 1508 (NH); $\delta_H$(500 MHz, $CDCl_3$) 7.07 (1H, d, J 5.5, CHNH), 6.65-6.44 (1H, br m, $CH_2NH$), 4.43 (1H, dd, J 11, 5.5, CHNH), 3.24-3.17 (2H, m, $CH_2NH$), 2.24 (2H, br s, adamantane CH), 2.20 (2H, br s, adamantane CH), 2.12-2.03 (4H, m, adamantane CH), 2.02-1.91 (2H, m, 2×lactam, ring CH), 1.85-1.72 (6H, m, 2×ring CH+4×adamantane CH), 1.66-1.55 (2H, m, 2×adamantane CH) and 1.45-1.31 (2H, m, 2×ring CH); $\delta_C$ (125 MHz, CDCl$_3$) 175.9, 174.9 (CO), 67.4 (CCl), 51.9 (NHCHCO), 48.6, 46.2 (×2) (3×CH$_2$ adamantane), 44.5 (CCO), 42.1 (CH$_2$N), 37.4, 37.3, 34.5 (3×CH$_2$ adamantane), 31.5 (CH$_2$ lactam), 31.1 (2×CH adamantane), 28.8, 27.9 (CH$_2$ lactam); m/z (MH$^+$C$_{17}$H$_{26}$N$_2$O$_2$Cl requires 325.1683) 325.1696.

Example 9

(S)-3-(3',5'-Dimethyl-1'-adamantanecarbonyl)amino-caprolactam (S)-3-amino-caprolactam hydrochloride 2 (1 mmol) and Na$_2$CO$_3$ (3 mmol) in water (15 ml) were added to a solution of 3,5-dimethyl-1-adamantanecarbonyl chloride (1 mmol) in dichloromethane (15 ml) at ambient temperature and the reaction was stirred for 12 hours. The organic layer was then separated and the aqueous phase was extracted with additional dichloromethane (2×25 ml). The combined organic layers were dried over Na$_2$CO$_3$ and reduced in vacuo. The residue was recrystallised from hexane to give (S)-3-(3',5'-dimethyl-1'-adamantanecarbonyl)amino-caprolactam (200 mg, 63%); m.p. 157-158° C.; $[\alpha]_D^{25}$ (c=0.5, CHCl$_3$)+26.8; $v_{max}$/cm$^{-1}$ (NH), 1647 (CO), 1548 (NH); $\delta_H$ (500 MHz, CDCl$_3$) 7.05 (1H, d, J 5.0, CHNH), 6.49-6.24 (1H, br m, CH$_2$NH), 4.45 (1H, ddd, J 11, 5.5, 1.5, CHNH), 3.30-3.16 (2H, m, CH$_2$NH), 2.12-2.07 (1H, m, adamantane CH), 2.04-1.90 (2H, m, 2×lactam ring CH), 1.86-1.73 (2H, m, 2×lactam ring CH), 1.67 (2H, br s, 2×adamantane CH), 1.51-1.26 (10H, br m, 8× adamantane CH+2×lactam ring CH) 1.17-1.09 (2H, m, adamantane CH) and 0.81 (6H, s, 2×CH$_3$); $\delta_C$ (125 MHz, CDCl$_3$) 176.9, 176.0 (CO), 51.9 (NHCHCO), 50.6, 45.2 (×2), 42.7 (×2) (CH$_2$ adamantane), 42.4 (CCO), 42.1 (CH$_2$N), 37.7 (CH$_2$ adamantane), 31.6 (CH$_2$ lactam), 31.0 (2×CCH$_3$), 30.4, 29.3 (CH$_3$), 28.9 and 27.9 (CH$_2$ lactam); m/z (MH$^+$ C$_{19}$H$_{31}$N$_2$O$_2$ requires 319.2386) 319.2372.

Example 10

(S)-3-(3',5',7'-Trimethyl-1'-adamantanecarbonyl)amino-caprolactam (S)-3-amino-caprolactam hydrochloride 2 (1 mmol) and Na$_2$CO$_3$ (3 mmol) in water (15 ml) were added to a solution of 3,5,7-trimethyl-1-adamantanecarbonyl chloride (1 mmol) in dichloromethane (15 ml) at ambient temperature and the reaction was stirred for 12 hours. The organic layer was then separated and the aqueous phase was extracted with additional dichloromethane (2×25 ml). The combined organic layers were dried over Na$_2$CO$_3$ and reduced in vacuo. The residue was recrystallised from EtOAc/hexane to give (S)-3-(3',5',7'-trimethyl-1'-adamantanecarbonyl)amino-caprolactam (188 mg, 56%); m.p. 177-178° C.; $[\alpha]_D^{25}$ (c=0.5, CHCl$_3$)+25.6; $v_{max}$/cm$^{-1}$ 3377, 3220 (NH), 1677, 1623 (CO), 1514 (NH); $\delta_H$ (500 MHz, CDCl$_3$) 7.06 (1H, d, J 5.0, CHNH), 6.40-6.15 (1H, br m, CH$_2$NH), 4.46 (1H, ddd, J11, 5.5, 1.5, CHNH), 3.32-3.17 (2H, m, CH$_2$NH), 2.03-1.92 (2H, m, 2×lactam ring CH), 1.86-1.74 (2H, m, 2×lactam ring CH) 1.47-1.32 (8H, m, 2×ring CH+6×adamantane CH) 1.06 (3H, br d, J 12, 3×adamantane CHH), 1.04 (3H, br d, J 12, 3×adamantine CHH) and 0.83 (9H, s, 3×CH$_3$); $\delta_C$ (125 MHz, CDCl$_3$) 176.8, 176.0 (CO), 51.9 (NHCHCO), 50.0 (3×CH$_2$ adamantane), 44.6 (3×CH$_2$ adamantane), 43.4 (CCO), 42.1 (CH$_2$N), 31.8 (3×CCH$_3$), 31.7 (CH$_2$ lactam), 30.0 (3×CH$_3$), 28.9, 27.9 (CH$_2$ lactam); m/z (MH$^+$C$_{20}$H$_{33}$N$_2$O$_2$ requires 333.2542) 333.2528.

Pharmacological Study of the Products of the Invention
Inhibition of MCP-1 Induced Leukocyte Migration
Assay Principle The biological activity of the compounds of the current invention may be demonstrated using any of a broad range of functional assays of leukocyte migration in vitro, including but not limited to Boyden chamber and related transwell migration assays, under-agarose migration assays and direct visualisation chambers such as the Dunn Chamber.

For example, to demonstrate the inhibition of leukocyte migration in response to chemokines (but not other chemoattractants) the 96-well format micro transwell assay system from Neuroprobe (Gaithersburg, Md., USA) has been used. In principle, this assay consists of two chambers separated by a porous membrane. The chemoattractant is placed in the lower compartment and the cells are placed in the upper compartment. After incubation for a period at 37° C. the cells move towards the chemoattractant, and the number of cells in the lower compartment is proportional to the chemoattractant activity (relative to a series of controls).

This assay can be used with a range of different leukocyte populations. For example, freshly prepared human peripheral blood leukocytes may be used. Alternatively, leukocyte subsets may be prepared, including polymorphonuclear cells or lymphocytes or monocytes using methods well known to those skilled in the art such as density gradient centrifugation or magnetic bead separations. Alternatively, immortal cell lines which have been extensively validated as models of human peripheral blood leukocytes may be used, including, but not limited to THP-1 cells as a model of monocytes or Jurkat cells as model of naive T cells.

Although a range of conditions for the assay are acceptable to demonstrate the inhibition of chemokine-induced leukocyte migration, a specific example is hereby provided.
Materials The transwell migration systems are manufactured by Neuroprobe, Gaithersburg, Md., USA.

The plates used are ChemoTx plates (Neuroprobe 101-8) and 30 µl clear plates (Neuroprobe MP30).

Geys' Balanced Salt Solution is purchased from Sigma (Sigma G-9779).

Fatty acid-free BSA is purchased from Sigma (Sigma A-8806).

MTT, i.e. 3-(4,5-dimethylthiazol-2-yl)-2,5-diphenyltetrazolium bromide, is purchased from Sigma (Sigma M-5655).

RPMI-1640 without phenol red is purchased from Sigma (Sigma R-8755).

The THP-1 cell line (European Cell culture Collection) were used as the leukocyte cell population.
Test Protocol The following procedure is used for testing the invention compounds for MCP-1 induced leukocyte migration:

First, the cell suspension to be placed in the upper compartment is prepared. The THP-1 cells are pelleted by centrifugation (770×g; 4 mins) and washed with Geys Balanced Salt Solution with 1 mg/ml BSA (GBSS+BSA). This wash is then repeated, and the cells repelleted before being resuspended in a small volume of GBSS+BSA for counting, for example using a standard haemocytometer.

The volume of GBSS+BSA is then adjusted depending on the number of cells present so that the cells are at final density of 4.45×10$^6$ cells per ml of GBSS+BSA. This ensures that there are 100,000 THP-1 cells in each 25 µl of the solution that will be placed in the upper chamber of the plate.

To test a single compound for its ability to inhibit MCP-1 induced migration, it is necessary to prepare two lots of cells. The suspension of THP-1 cells at 4.45×10$^6$ cells/ml is divided into two pots. To one pot the inhibitor under test is added at an appropriate final concentration, in an appropriate vehicle (for example at 1 μM in not more than 1% DMSO). To the second pot an equal volume of GBSS+BSA plus vehicle as appropriate (e.g. not more than 1% DMSO) is added to act as a control.

Next, the chemoattractant solution to be placed in the lower compartment is prepared. MCP-1 is diluted in GBSS+BSA to give a final concentration of 25 ng/ml. This is divided into two pots, as for the cell suspension. To one pot, the test compound is added to the same final concentration as was added to the cell suspension, while to the other pot an equal volume of GBSS+BSA plus vehicle as appropriate (e.g. not more than 1% DMSO) is added.

Note that the volume of liquid that needs to be added to make the addition of the text compound needs to be taken into account, when establishing the final concentration of MCP-1 in the solution for the lower compartment and the final concentration of cells in the upper compartment.

Once the chemoattractant solutions for the lower wells and cell solution for the upper chambers have been prepared, the migration chamber should be assembled. Place 29 μl of the appropriate chemoattractant solution into the lower well of the chamber. Assays should be performed with at least triplicate determinations of each condition. Once all the lower chambers have been filled, apply the prous membrane to the chamber in accordance with the manufacturer's instructions. Finally, apply 25 μl of the appropriate cell solution to each upper chamber. A plastic lid is placed over the entire apparatus to prevent evaporation.

The assembled chamber is incubated at 37° C., 5% $CO_2$, for 2 hours. A suspension of cells in GBSS+BSA is also incubated under identical conditions in a tube. These cells will be used to construct a standard curve for determining the number of cells that have migrated to the lower chamber under each condition.

At the end of the incubation, the liquid cell suspension is gently removed from the upper chamber, and 20 μl of ice-cold 20 mM EDTA in PBS is added to the upper chamber, and the apparatus is incubated at 4° C. for 15 rains. This procedure causes any cells adhering to the underside of the membrane to fall into the lower chamber.

After this incubation the filter is carefully flushed with GBSS+BSA to wash off the EDTA, and then the filter is removed.

The number of cells migrated into the lower chamber under each condition can then be determined by a number of methods, including direct counting, labelling with fluorescent or radioactive markers or through the use of a vital dye. Typically, we utilise the vital dye MTT. 3 μl of stock MTT solution are added to each well, and then the plate is incubated at 37° C. for 1-2 hours during which time dehydrogenase enzymes within the cells convert the soluble MTT to an insoluble blue formazan product that can be quantified spectrophotometrically.

In parallel, an 8-point standard curve is set up. Starting with the number of cells added to each upper chamber (100,000) and going down in 2-fold serial dilutions in GBSS+BSA, the cells are added to a plate in 25 μl, with 3 μl of MTT stock solution added. The standard curve plate is incubated along side the migration plate.

At the end of this incubation, the liquid is carefully removed from the lower chambers, taking care not to disturb the precipitated formazan product. After allowing to air dry briefly, 20 μl of DMSO is added to each lower chamber to solubilise the blue dye, and absorbance at 595 nm is determined using a 96-well plate reader. The absorbance of each well is then interpolated to the standard curve to estimate the number of cells in each lower chamber.

The MCP-1 stimulated migration is determined by subtracting the average number of cells that reached the lower compartment in wells where no MCP-1 was added from the average number of cells that reached the lower compartment where MCP-1 was present at 25 ng/ml.

The impact of the test substance is calculated by comparing the MCP-1-induced migration which occurred in the presence or absence of various concentrations of the test substance. Typically, the inhibition of migration is expressed as a percentage of the total MCP-1 induced migration which was blocked by the presence of the compound. For most compounds, a dose-response graph is constructed by determining the inhibition of MCP-1 induced migration which occurs at a range of different compound concentrations (typically ranging from 1 nM to 1 μM or higher in the case of poorly active compounds). The inhibitory activity of each compound is then expressed as the concentration of compound required to reduce the MCP-1-induced migration by 50% (the $ED_{50}$ concentration).

Results

The compounds of examples 1 to 8 and 10 were tested and were shown to have an $ED_{50}$ of 100 nM or less in this test.

Enantioselectivity

The (S)- and (R)-enantiomers of two different members of the aminocaprolactam series can be synthesised to determine whether the biological activity showed enantioselectivity.

The dose-response curves for each of the compounds as inhibitors of MCP-1 induced THP-1 cell migration can be determined using the transwell migration assay.

For the application of the compounds of the present invention as anti-inflammatory agents in vivo it is preferable to use the pure (S)-enantiomer of the compound, rather than the racemic mixture of the two enantiomers or the pure (R)-enantiomer.

What is claimed is:

1. A method of treating an inflammatory disorder comprising administering to a subject in need thereof a compound of formula (I) or a pharmaceutically acceptable salt thereof:

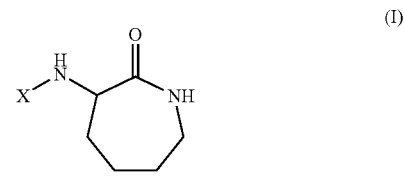

(I)

wherein

X is $—CO—Y—(R^1)_n$ or $SO_2—Y—(R^1)_n$;

Y is a cycloalkyl, polycycloalkyl, or cycloalkenyl group, wherein Y includes no more than 10 carbon atoms;

each $R^1$ is independently hydrogen, an alkyl or alkylamino radical of 1 to 20 carbon atoms, fluoro, chloro, bromo, iodo, or hydroxy radical;

n is any integer from 1 to m, where m is the maximum number of substitutions permissible on the cyclo-group Y; and wherein the inflammatory disorder is selected from the group consisting of:

rheumatoid arthritis, asthma, and multiple sclerosis.

2. The method of claim 1 wherein the compound of formula (I) is a compound of formula (I') or a pharmaceutically acceptable salt thereof:

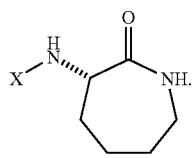

(I')

3. The method of claim 1 wherein the ring or rings of Y constrain the bond angles at the alpha-carbon at the 2-position relative to the amide carbonyl of the —CO—Y—(R$^1$)$_n$ group or at the 1-position relative to the sulfonamide sulfonyl group of the —SO$_2$—Y—(R$^1$)$_n$ group of formula (I) such that the alpha-carbon is essentially tetrahedral.

4. The method of claim 1 wherein Y is an adamantyl, adamantanemethyl, bicyclooctyl, cyclohexyl, or cyclopropyl group.

5. The method of claim 1 wherein the substituent R$^1$ is not a straight chain alkyl group.

6. The method of claim 1 wherein the substituent R$^1$ is not an alkyl group.

7. The method of claim 1 wherein the substituent R$^1$ is hydrogen.

8. The method of claim 1 wherein each R$^1$ is independently H, or an alkyl or alkylamino radical of 10 to 18 carbon atoms.

9. The method of claim 1 wherein the compound of formula (I) is selected from:
(S)-3-(Cyclohexanecarbonyl)amino-caprolactam;
(S)-3-(1'-methylcyclohexanecarbonyl)amino-caprolactam;
(S)-3-(Cyclohex-1'-enecarbonyl)amino-caprolactam;
(S)-3-(trans-4'-pentylcyclohexane-1-carbonyl)amino-caprolactam;
(S)-3-(4'-pentyl[2,2,2]bicyclo-octane-1-carbonyl)amino-caprolactam;
(S)-3-(1'-Adamantanecarbonyl)amino-caprolactam;
(S)-3-(1'-Adamantanylmethanecarbonyl)amino-caprolactam;
(S)-3-(3'-chloro-1'-adamantanecarbonyl)amino-caprolactam;
(S)-3-(3',5'-Dimethyl-1'-adamantanecarbonyl)amino-caprolactam;
(S)-3-(3',5',7'-Trimethyl-1'-adamantanecarbonyl)amino-caprolactam;
(S)-3-(Cyclohexanesulfonyl)amino-caprolactam;
(S)-3-(1'-methylcyclohexanesulfonyl)amino-caprolactam;
(S)-3-(Cyclohex-1'-enesulfonyl)amino-caprolactam;
(S)-3-(trans-4'-pentylcyclohexane-1-sulfonyl)amino-caprolactam;
(S)-3-(4'-pentyl[2,2,2]bicyclo-octane-1-sulfonyl)amino-caprolactam;
(S)-3-(1'-Adamantanesulfonyl)amino-caprolactam;
(S)-3-(1'-Adamantanylmethanesulfonyl)amino-caprolactam;
(S)-3-(3'-chloro-1'-adamantanesulfonyl)amino-caprolactam;
(S)-3-(3',5'-Dimethyl-1'-adamantanesulfonyl)amino-caprolactam;
(S)-3-(3',5',7'-Trimethyl-1'-adamantanesulfonyl)amino-caprolactam;
or a pharmaceutically acceptable salt thereof.

10. The method of claim 1 wherein the inflammatory disorder is asthma.

11. The method of claim 1 wherein the inflammatory disorder is rheumatoid arthritis.

12. A method of treatment, amelioration or prophylaxis of the symptoms of an inflammatory disease, comprising administering to a patient in need thereof an anti-inflammatory amount of a compound of formula (I) or a pharmaceutically acceptable salt thereof:

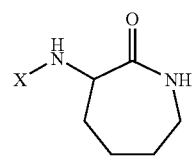

(I)

wherein
X is —CO—Y—(R$^1$)$_n$ or SO$_2$—Y—(R$^1$)$_n$;
Y is a cycloalkyl, polycycloalkyl, or cycloalkenyl group, wherein Y includes no more than 10 carbon atoms;
each R$^1$ is independently hydrogen, an alkyl or alkylamino radical of 1 to 20 carbon atoms, fluoro, chloro, bromo, iodo, or hydroxy radical;
n is any integer from 1 to m, where m is the maximum number of substitutions permissible on the cyclo-group Y; and
wherein the inflammatory disorder is selected from the group consisting of:
rheumatoid arthritis, asthma, and multiple sclerosis.

13. The method of claim 12 wherein the compound of formula (I) is a compound of formula (I') or a pharmaceutically acceptable salt thereof:

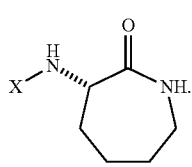

(I')

14. The method of claim 12 wherein the compound of formula (I) is selected from:
(S)-3-(Cyclohexanecarbonyl)amino-caprolactam;
(S)-3-(1'-methylcyclohexanecarbonyl)amino-caprolactam;
(S)-3-(Cyclohex-1'-enecarbonyl)amino-caprolactam;
(S)-3-(trans-4'-pentylcyclohexane-1-carbonyl)amino-caprolactam;
(S)-3-(4'-pentyl[2,2,2]bicyclo-octane-1-carbonyl)amino-caprolactam;
(S)-3-(1'-Adamantanecarbonyl)amino-caprolactam;
(S)-3-(1'-Adamantanylmethanecarbonyl)amino-caprolactam;
(S)-3-(3'-chloro-1'-adamantanecarbonyl)amino-caprolactam;
(S)-3-(3',5'-Dimethyl-1'-adamantanecarbonyl)amino-caprolactam;
(S)-3-(3',5',7'-Trimethyl-1'-adamantanecarbonyl)amino-caprolactam;
(S)-3-(Cyclohexanesulfonyl)amino-caprolactam;
(S)-3-(1'-methylcyclohexanesulfonyl)amino-caprolactam;
(S)-3-(Cyclohex-1'-enesulfonyl)amino-caprolactam;
(S)-3-(trans-4'-pentylcyclohexane-1-sulfonyl)amino-caprolactam;

(S)-3-(4'-pentyl[2,2,2]bicyclo-octane-1-sulfonyl)amino-caprolactam;
(S)-3-(1'-Adamantanesulfonyl)amino-caprolactam;
(S)-3-(1'-Adamantanylmethanesulfonyl)amino-caprolactam;
(S)-3-(3'-chloro-1'-adamantanesulfonyl)amino-caprolactam;
(S)-3-(3',5'-Dimethyl-1'-adamantanesulfonyl)amino-caprolactam;
(S)-3-(3',5',7'-Trimethyl-1'-adamantanesulfonyl)amino-caprolactam;
or a pharmaceutically acceptable salt thereof.

15. The method of claim 12 wherein the inflammatory disease is asthma.

16. The method of claim 12 wherein the inflammatory disease is rheumatoid arthritis.

17. The method of claim 13 wherein the compound of formula (I') is (S)-3-(1'-adamantanecarbonyl)amino-caprolactam, or a pharmaceutically acceptable salt thereof.

18. The method of claim 13 wherein the inflammatory disease is asthma.

19. The method of claim 13 wherein the inflammatory disease is rheumatoid arthritis.

20. The method of claim 2 wherein the compound of formula (I') is (S)-3-(1'-adamantanecarbonyl)amino-caprolactam, or a pharmaceutically acceptable salt thereof.

21. The method of claim 2 wherein the inflammatory disorder is asthma.

22. The method of claim 2 wherein the inflammatory disorder is rheumatoid arthritis.

* * * * *